(12) United States Patent
Biedermann et al.

(10) Patent No.: US 12,096,963 B2
(45) Date of Patent: Sep. 24, 2024

(54) COUPLING ASSEMBLY FOR COUPLING A ROD TO A BONE ANCHORING ELEMENT AND BONE ANCHORING DEVICE WITH SUCH A COUPLING ASSEMBLY

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 439 days.

(21) Appl. No.: 17/376,606

(22) Filed: Jul. 15, 2021

(65) Prior Publication Data

US 2022/0000521 A1  Jan. 6, 2022

Related U.S. Application Data

(63) Continuation of application No. 16/443,129, filed on Jun. 17, 2019, now Pat. No. 11,090,089, which is a (Continued)

(30) Foreign Application Priority Data

Feb. 11, 2013  (EP) ..................................... 13154823

(51) Int. Cl.
*A61B 17/70*  (2006.01)
(52) U.S. Cl.
CPC ................................ *A61B 17/7037* (2013.01)
(58) Field of Classification Search
CPC .............. A61B 17/7032; A61B 17/7035–7037
See application file for complete search history.

(56) References Cited

U.S. PATENT DOCUMENTS 5,672,176 A  9/1997 Biedermann et al.
6,010,503 A  1/2000 Richelsoph et al.
(Continued)

FOREIGN PATENT DOCUMENTS

CN    1359660 A     7/2002
EP    0 947 174 A2  10/1999
(Continued)

OTHER PUBLICATIONS

European Search Report for European Application No. 09002468.8, Applicant Biedermann Motech GmbH, European Search Report dated May 5, 2009 and mailed May 18, 2009 (6 pgs.).
(Continued)

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A coupling assembly for coupling a rod to a bone anchoring element includes a receiving part with an accommodation space defining an opening for inserting and accommodating a head of the bone anchoring element, and a pressure element having a cap portion configured to hold the head. In an inserting position, the cap portion of the pressure element is expandable in the accommodation space of the receiving part, and a first retaining element is configured to prevent the pressure element from moving towards a first end of the receiving part. In a pre-locking position, the head is held in the cap portion of the pressure element and is pivotable in the receiving part, while the cap portion is restricted from expanding to prevent removal of the head, and where a second retaining element is configured to prevent the pressure element from moving from the pre-locking position towards the inserting position.

25 Claims, 8 Drawing Sheets

Related U.S. Application Data continuation of application No. 15/854,174, filed on Dec. 26, 2017, now Pat. No. 10,357,289, which is a continuation of application No. 14/177,145, filed on Feb. 10, 2014, now Pat. No. 9,895,170.

(60) Provisional application No. 61/763,426, filed on Feb. 11, 2013.

(56) References Cited

U.S. PATENT DOCUMENTS

| | | | |
|---|---|---|---|
| 6,063,090 | A | 5/2000 | Schläpfer |
| 6,132,432 | A | 10/2000 | Richelsoph |
| 6,355,040 | B1 | 3/2002 | Richelsoph et al. |
| 6,368,321 | B1 | 4/2002 | Jackson |
| 6,471,705 | B1 | 10/2002 | Biedermann et al. |
| 7,144,396 | B2 | 12/2006 | Shluzas |
| 7,291,151 | B2 | 11/2007 | Alvarez |
| 7,322,981 | B2 | 1/2008 | Jackson |
| 7,604,655 | B2 | 10/2009 | Warnick |
| 7,682,377 | B2 | 3/2010 | Konieczynski et al. |
| 8,083,776 | B2 | 12/2011 | Alvarez |
| 8,444,681 | B2 | 5/2013 | Jackson et al. |
| 8,663,290 | B2 | 3/2014 | Doubler et al. |
| 8,814,911 | B2 | 8/2014 | Jackson |
| 8,926,671 | B2 | 1/2015 | Biedermann et al. |
| 9,895,170 | B2 | 2/2018 | Biedermann et al. |
| 10,357,289 | B2 | 7/2019 | Biedermann et al. |
| 2002/0082602 | A1 | 6/2002 | Biedermann et al. |
| 2003/0153911 | A1 | 8/2003 | Shluzas |
| 2003/0167058 | A1 | 9/2003 | Shluzas |
| 2005/0137594 | A1 | 6/2005 | Doubler et al. |
| 2006/0089644 | A1 | 4/2006 | Felix |
| 2006/0161153 | A1 | 7/2006 | Hawkes et al. |
| 2006/0173456 | A1 | 8/2006 | Hawkes et al. |
| 2006/0276791 | A1 | 12/2006 | Shluzas |
| 2007/0118117 | A1 | 5/2007 | Altarac et al. |
| 2007/0123862 | A1* | 5/2007 | Warnick ............. A61B 17/7032 606/261 |
| 2007/0161996 | A1 | 7/2007 | Biedermann et al. |
| 2007/0161999 | A1 | 7/2007 | Biedermann et al. |
| 2007/0270813 | A1 | 11/2007 | Garamszegi |
| 2007/0288004 | A1 | 12/2007 | Alvarez |
| 2008/0009862 | A1 | 1/2008 | Hoffman |
| 2008/0147129 | A1 | 6/2008 | Biedermann et al. |
| 2008/0154315 | A1 | 6/2008 | Jackson |
| 2008/0183215 | A1 | 7/2008 | Altarac et al. |
| 2008/0234761 | A1 | 9/2008 | Jackson |
| 2008/0243193 | A1 | 10/2008 | Ensign et al. |
| 2008/0249576 | A1 | 10/2008 | Hawkes et al. |
| 2008/0269809 | A1 | 10/2008 | Garamszegi |
| 2008/0294202 | A1 | 11/2008 | Peterson et al. |
| 2008/0294203 | A1 | 11/2008 | Kovach et al. |
| 2009/0012567 | A1 | 1/2009 | Biedermann et al. |
| 2009/0018591 | A1 | 1/2009 | Hawkes et al. |
| 2009/0036934 | A1 | 2/2009 | Biedermann et al. |
| 2009/0062865 | A1 | 3/2009 | Schumacher |
| 2009/0062867 | A1 | 3/2009 | Schumacher |
| 2009/0105716 | A1 | 4/2009 | Barrus |
| 2009/0149887 | A1 | 6/2009 | Schlaepfer et al. |
| 2010/0114170 | A1 | 5/2010 | Barrus et al. |
| 2010/0114171 | A1 | 5/2010 | Boachie-Adjei et al. |
| 2010/0137918 | A1 | 6/2010 | Wilcox et al. |
| 2010/0145394 | A1 | 6/2010 | Harvey et al. |
| 2010/0152787 | A1 | 6/2010 | Walsh et al. |
| 2010/0198272 | A1 | 8/2010 | Keyer et al. |
| 2010/0234902 | A1* | 9/2010 | Biedermann ...... A61B 17/7037 606/305 |
| 2011/0202094 | A1 | 8/2011 | Pereira et al. |
| 2011/0213424 | A1 | 9/2011 | Biedermann et al. |
| 2012/0035670 | A1 | 2/2012 | Jackson et al. |
| 2012/0046701 | A1 | 2/2012 | Gennari et al. |
| 2012/0143266 | A1* | 6/2012 | Jackson ............. A61B 17/7032 606/328 |
| 2012/0165874 | A1 | 6/2012 | Biedermann et al. |
| 2012/0179209 | A1 | 7/2012 | Biedermann et al. |
| 2012/0179210 | A1 | 7/2012 | Garamszegi |
| 2012/0179211 | A1 | 7/2012 | Biedermann et al. |
| 2012/0209335 | A1 | 8/2012 | Termyna et al. |
| 2012/0209336 | A1 | 8/2012 | Jackson et al. |
| 2013/0046345 | A1 | 2/2013 | Jones et al. |
| 2013/0066376 | A1 | 3/2013 | Biedermann et al. |
| 2013/0197586 | A1 | 8/2013 | Matthis et al. |
| 2013/0226243 | A1 | 8/2013 | Kraus |
| 2013/0338721 | A1 | 12/2013 | Biedermann et al. |
| 2013/0345754 | A1 | 12/2013 | Doubler et al. |
| 2014/0031880 | A1 | 1/2014 | Biedermann et al. |
| 2014/0046374 | A1 | 2/2014 | Asaad et al. |
| 2014/0107708 | A1 | 4/2014 | Biedermann et al. |
| 2014/0142634 | A1* | 5/2014 | Schlaepfer ........... A61B 17/704 29/428 |
| 2014/0188174 | A1 | 7/2014 | Biedermann et al. |
| 2014/0236239 | A1 | 8/2014 | Biedermann et al. |
| 2014/0277157 | A1 | 9/2014 | Chandanson et al. |
| 2014/0277161 | A1 | 9/2014 | Spratt et al. |
| 2015/0025579 | A1 | 1/2015 | Biedermann et al. |
| 2015/0032162 | A1 | 1/2015 | Biedermann et al. |
| 2015/0045835 | A1 | 2/2015 | Kim |
| 2015/0080960 | A1 | 3/2015 | Biedermann et al. |
| 2015/0088202 | A1 | 3/2015 | Charvet |
| 2015/0134018 | A1 | 5/2015 | Ziolo et al. |
| 2015/0142059 | A1 | 5/2015 | Biedermann et al. |
| 2015/0148848 | A1 | 5/2015 | Doubler et al. |
| 2015/0173816 | A1 | 6/2015 | Biedermann et al. |
| 2015/0196338 | A1 | 7/2015 | Biedermann et al. |
| 2015/0201972 | A1 | 7/2015 | Doubler et al. |
| 2015/0230829 | A1 | 8/2015 | Harris et al. |
| 2016/0045228 | A1 | 2/2016 | Biedermann et al. |
| 2016/0256199 | A1 | 9/2016 | Biedermann et al. |
| 2017/0196606 | A1 | 7/2017 | Cianfrani et al. |

FOREIGN PATENT DOCUMENTS

| | | |
|---|---|---|
| EP | 1 749 489 A1 | 2/2007 |
| EP | 1 923 011 A1 | 5/2008 |
| EP | 2 301 458 A1 | 3/2011 |
| JP | 8-257035 | 10/1996 |
| JP | 10-225467 A | 8/1998 |
| JP | 11-318933 | 11/1999 |
| JP | 2001-505469 A | 4/2001 |
| JP | 2007-105472 A | 4/2007 |
| JP | 2008-541880 A | 11/2008 |
| JP | 2011-67628 A | 4/2011 |
| JP | 2013-500127 A | 1/2013 |
| WO | WO 2006/127992 | 11/2006 |
| WO | WO 2007/038350 A2 | 4/2007 |
| WO | WO 2007/117366 A2 | 10/2007 |
| WO | WO 2009/014540 A1 | 1/2009 |
| WO | WO 2011/043805 A1 | 4/2011 |

OTHER PUBLICATIONS

European Search Report and Opinion issued by the EPO for EP 13154823.2 on Jun. 21, 2013 (8 pages).

Korean Office action for Application No. 10-2010-0013817, dated Feb. 18, 2016, and English translation (12 pages).

Japanese Office action dated Dec. 6, 2016 for Application No. 2014-021386 (3 pages).

Non-Final Office action for U.S. Appl. No. 12/709,375, dated Dec. 5, 2011, 7 pages.

Final Office action for U.S. Appl. No. 12/709,375, dated Jul. 10, 2012, 6 pages.

Non-Final Office action for U.S. Appl. No. 12/709,375, dated Sep. 13, 2013, 6 pages.

Final Office action for U.S. Appl. No. 12/709,375, dated Jun. 4, 2014, 5 pages.

Non-Final Office action for U.S. Appl. No. 14/517,624, dated Aug. 10, 2017, 12 pages.

Non-Final Office action for U.S. Appl. No. 15/156,274, dated Sep. 14, 2016, 8 pages.

Final Office action for U.S. Appl. No. 15/156,274, dated Dec. 29, 2016, 9 pages.

(56) References Cited

OTHER PUBLICATIONS

Non-Final Office action for U.S. Appl. No. 15/156,274, dated Jun. 30, 2017, 7 pages.

* cited by examiner

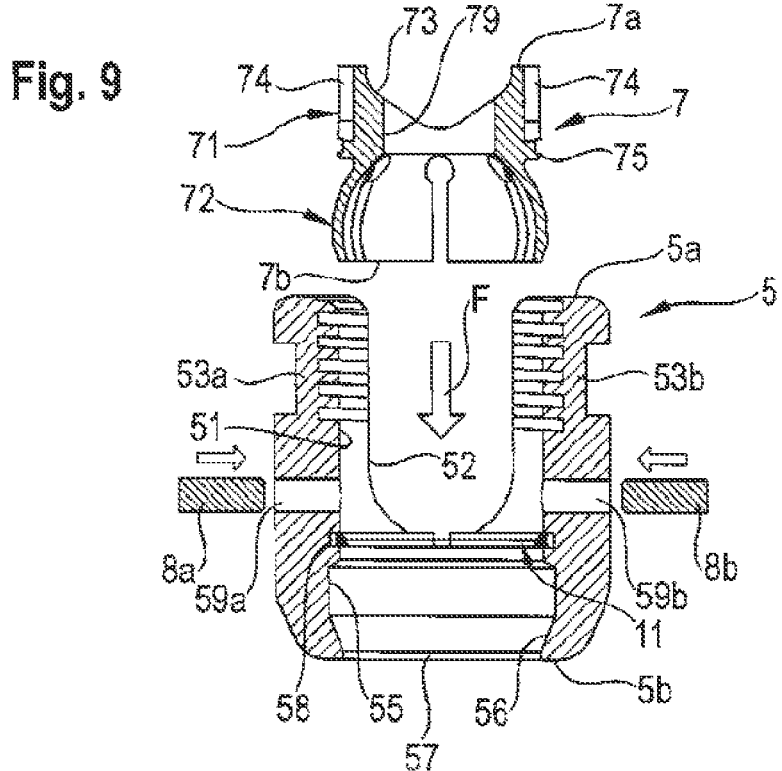
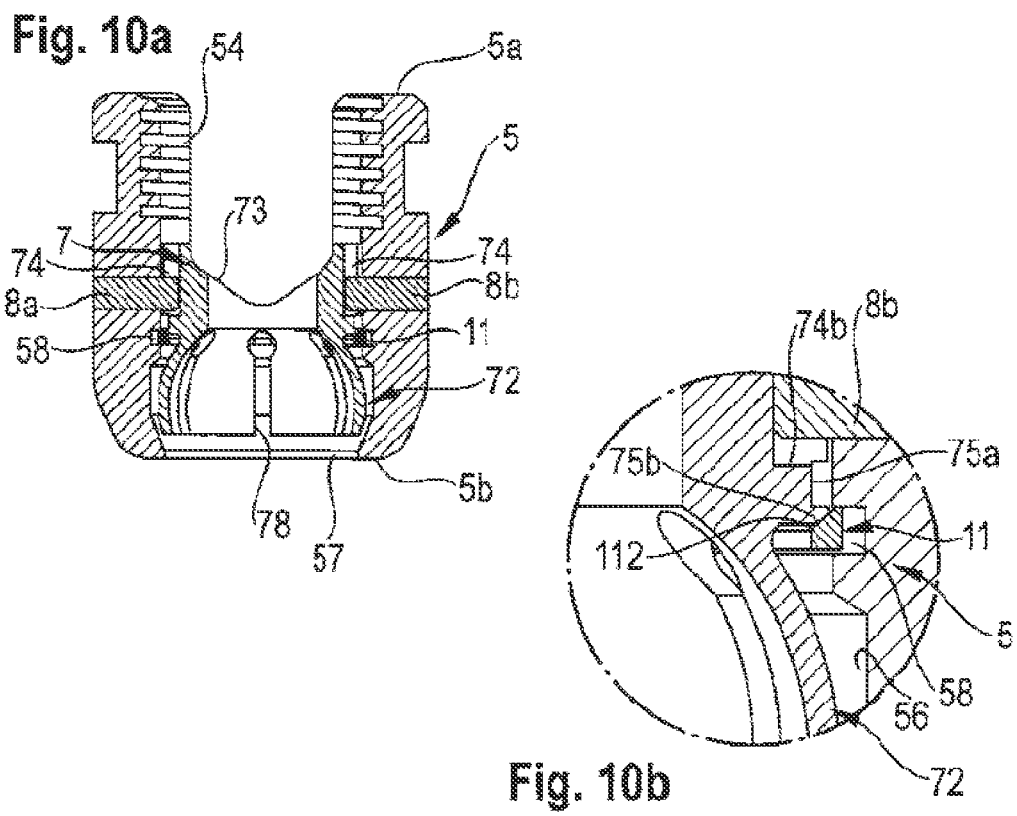

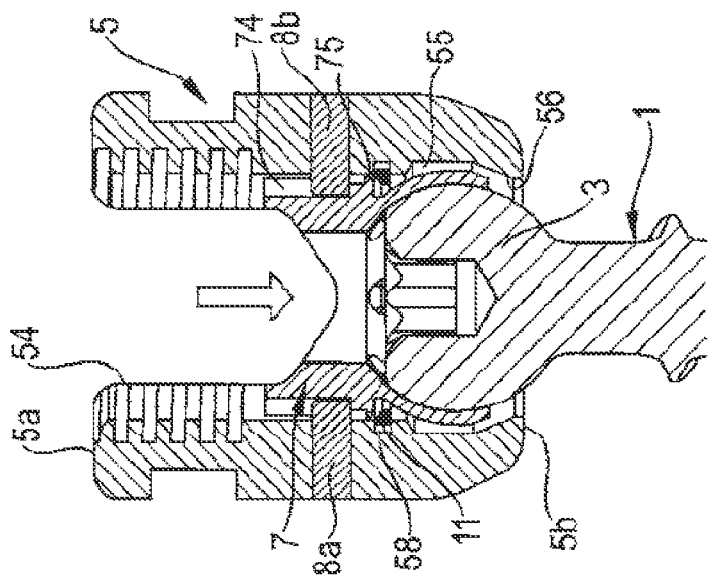
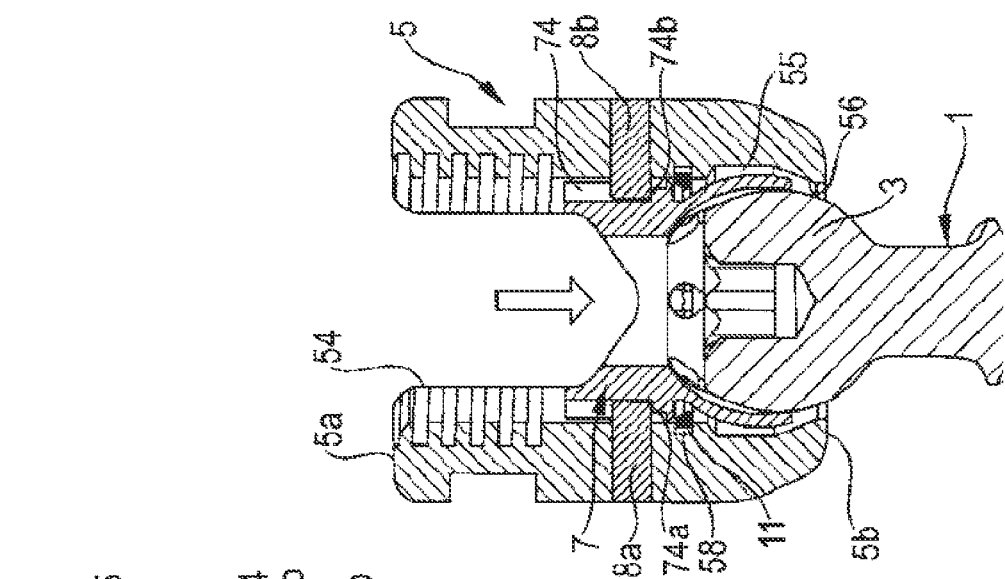
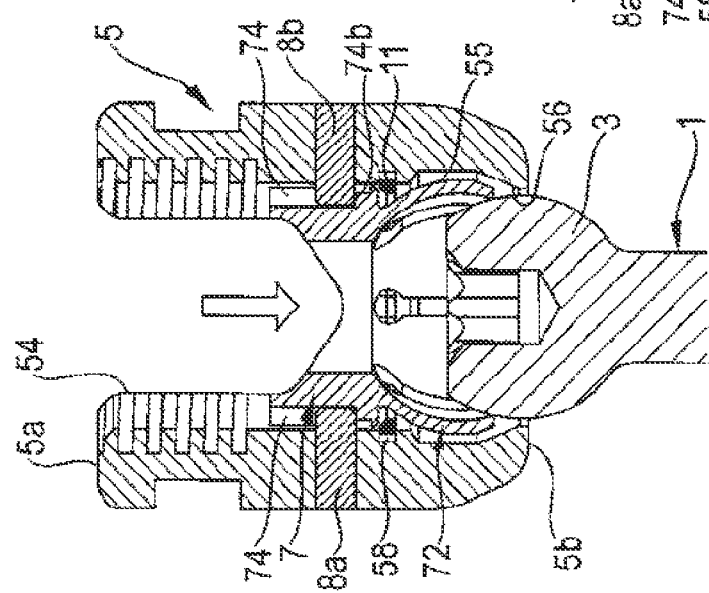

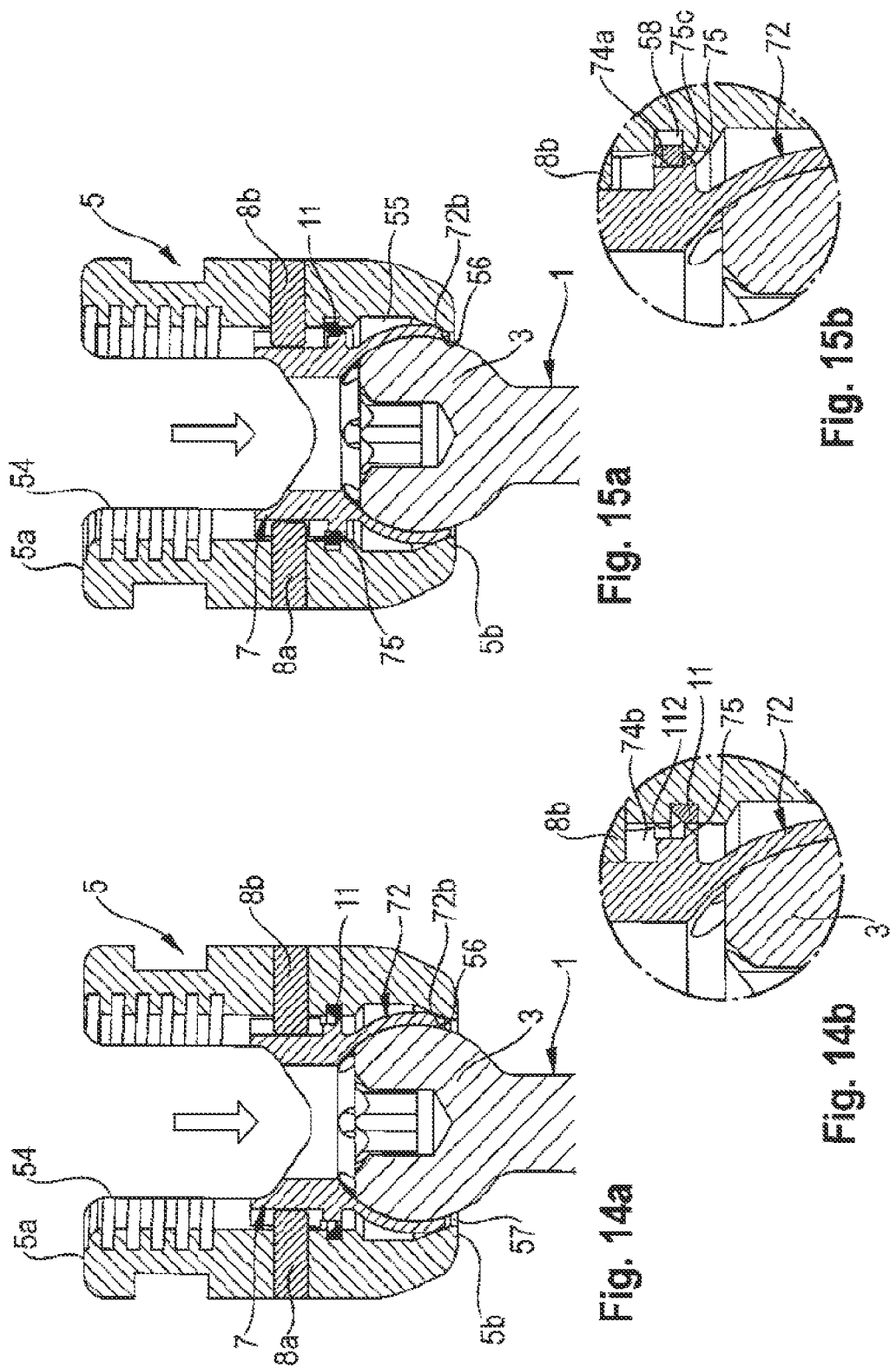

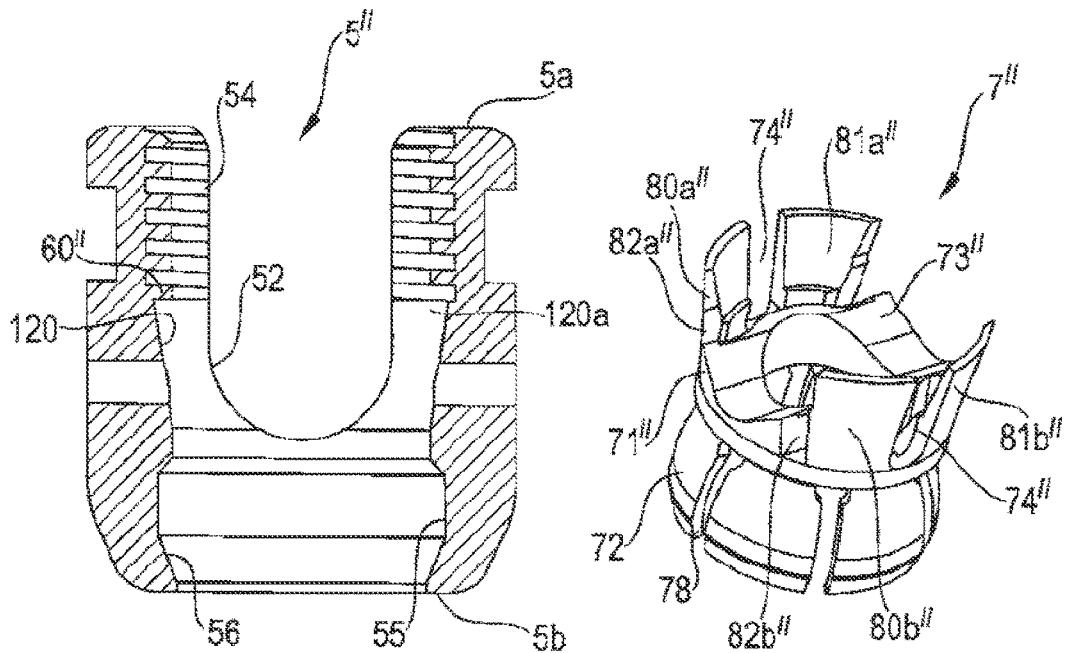
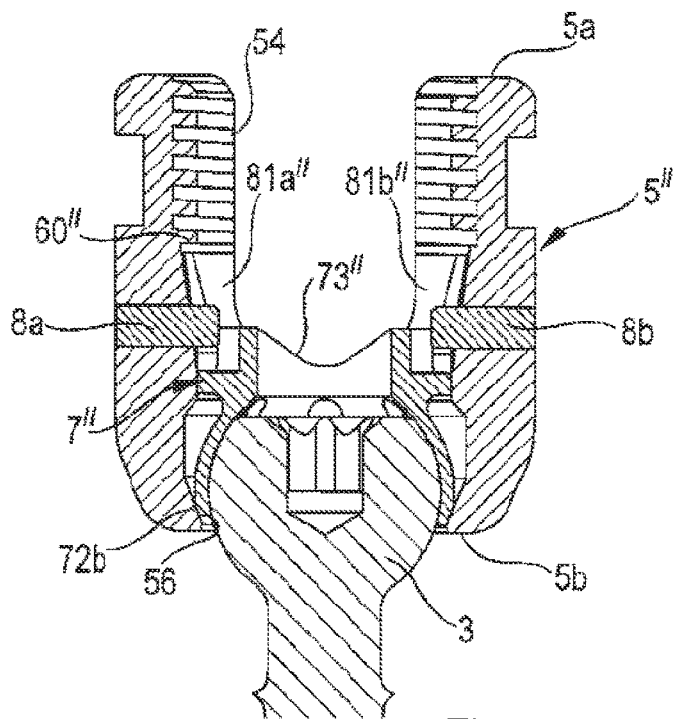

COUPLING ASSEMBLY FOR COUPLING A ROD TO A BONE ANCHORING ELEMENT AND BONE ANCHORING DEVICE WITH SUCH A COUPLING ASSEMBLY

CROSS-REFERENCE TO RELATED APPLICATIONS

This application is a continuation of U.S. patent application Ser. No. 16/443,129, filed Jun. 17, 2019, which is a continuation of U.S. patent application Ser. No. 15/854,174, filed Dec. 26, 2017, now U.S. Pat. No. 10,357,289, which is a continuation of U.S. patent application Ser. No. 14/177,145, filed Feb. 10, 2014, now U.S. Pat. No. 9,895,170, which claims the benefit of U.S. Provisional Patent Application Ser. No. 61/763,426, filed Feb. 11, 2013, the contents of which are hereby incorporated by reference in their entirety, and claims priority from European Patent Application EP 13154823.2, filed Feb. 11, 2013, the contents of which are hereby incorporated by reference in their entirety.

BACKGROUND

Field

The invention relates to a coupling assembly for coupling a rod to a bone anchoring element, and to a bone anchoring device with such a coupling assembly. The coupling assembly includes a receiving part and a pressure element located at least partially in an accommodation space of the receiving part. The pressure element has a flexible portion to clamp a head of the bone anchoring element. The pressure element can assume in the receiving part an insertion position where insertion and removal of the head is permitted, a locking position where the head is locked in the receiving part, and a pre-locking position where the head is pivotable but is prevented from removal from the receiving part.

Description of Related Art

US 2010/0234902 A1 describes a receiving part for receiving a rod for coupling the rod to a bone anchoring element, wherein the receiving part includes a receiving part body with a channel for receiving a rod and an accommodation space for the head of a bone anchoring element. The accommodation space has a bottom opening for inserting the head, and a pressure element is at least partially provided in the accommodation space to clamp the head. The pressure element is movable along a longitudinal axis of the receiving part body from an inserting position to insert the head, to a pre-locking position to clamp the head in the receiving part by a pre-stress exerted by the pressure element, and to a locking position to lock the head in the receiving part.

SUMMARY

It is an object of the invention to provide an improved coupling assembly for coupling a rod to a bone anchoring element, and a bone anchoring device with such a coupling assembly that can be more safely handled during surgery.

The bone anchoring device is a bottom loading type bone anchoring device, wherein the head of the bone anchoring element is inserted into the receiving part from the bottom end. Once the pressure element is mounted to or inserted into the receiving part, the pressure element can be prevented from escaping from the top end of the receiving part by a first retaining member. After the head has been inserted into the receiving part and into a flexible cap portion of the pressure element, the head can be prevented by a second retaining member from being inadvertently pulled out through the bottom end of the receiving part. The first retaining member also holds the pressure element with respect to the receiving part in an aligned position to permit the insertion of a rod. The second retaining member may also hold the pressure element in a pre-locking position to prevent a further upward movement of the pressure element once the head is inserted. By the second retaining member, the step of aligning the coupling assembly with the rod, and generally the handling of the bone anchoring device, may be made safer because, for example, an inadvertent removal of the head through the lower opening is prevented.

The bone anchoring device is particularly useful for methods of in-situ assembly of the bone anchoring device, wherein the bone anchoring element is first implanted into the bone, and then the coupling assembly is mounted to the head of the bone anchoring element.

The coupling assembly can be part of a modular bone anchoring system, wherein a plurality of bone anchoring elements that differ in terms of their shank length, shank diameter, bone anchoring features, such as threads, barbs, etc., shank types, such as solid shanks, cannulated shanks with openings in the shank wall, etc., can be provided with one type of coupling assembly, to allow for an "on demand" assembly of a specific or appropriate bone anchoring element with the coupling assembly.

BRIEF DESCRIPTION OF THE DRAWINGS

Further features and advantages of the invention will become apparent from the description of embodiments by means of the accompanying drawings. In the drawings:

FIG. 9 shows a cross-sectional view of a step of mounting the pressure element into the receiving part, which includes the second retaining member, according to the first embodiment;

FIG. 10a shows a cross-sectional view of the pressure element mounted to the receiving part after the step shown in FIG. 9;

FIG. 10b shows an enlarged cross-sectional view of a portion of FIG. 10a;

FIGS. 11 to 13 show cross-sectional views of steps of inserting a head of a bone anchoring element into the receiving part and the pressure element according to the first embodiment;

FIG. 14a shows a cross-sectional view of a step of moving the pressure element downward with the head being inserted according to the first embodiment;

FIG. 14b shows an enlarged cross-sectional view of a portion of FIG. 14a;

FIG. 15a shows a cross-sectional view of the coupling assembly with the pressure element in the pre-locking position and retained by the second retaining member according to the first embodiment;

FIG. 15b shows an enlarged cross-sectional view of a portion of FIG. 15a;

FIG. 23 shows a cross-sectional view of a receiving part according to a third embodiment, the cross-section taken in a plane through a central axis of the receiving part and perpendicular to an axis of an inserted rod;

FIG. 24 shows a perspective view of a pressure element according to the third embodiment; and FIG. 25 shows a cross-sectional view of the coupling assembly with the head inserted and the pressure element in a pre-locking position according to the third embodiment.

DETAILED DESCRIPTION

Figure 1:
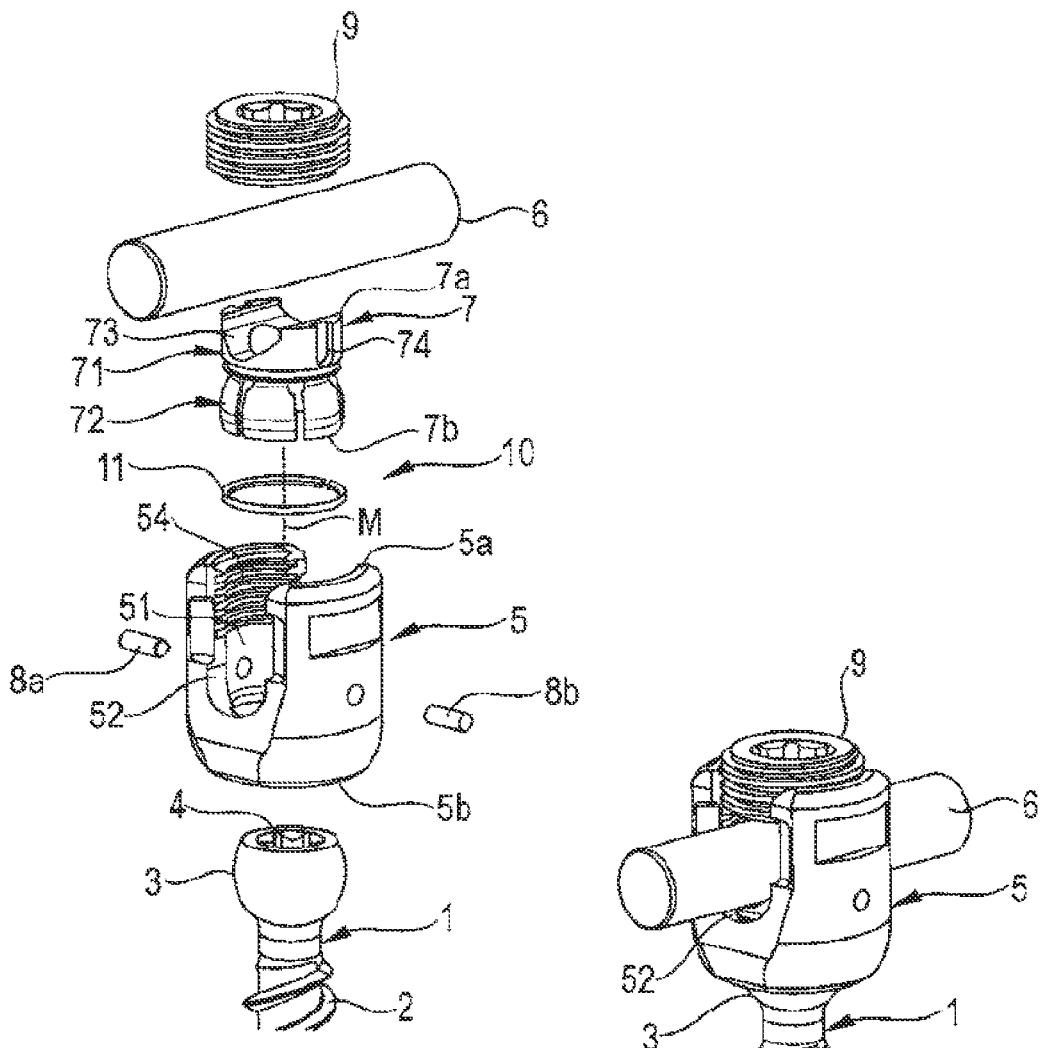
FIG. 1 shows a perspective exploded view of a first embodiment of a bone anchoring device.
Figure 2:
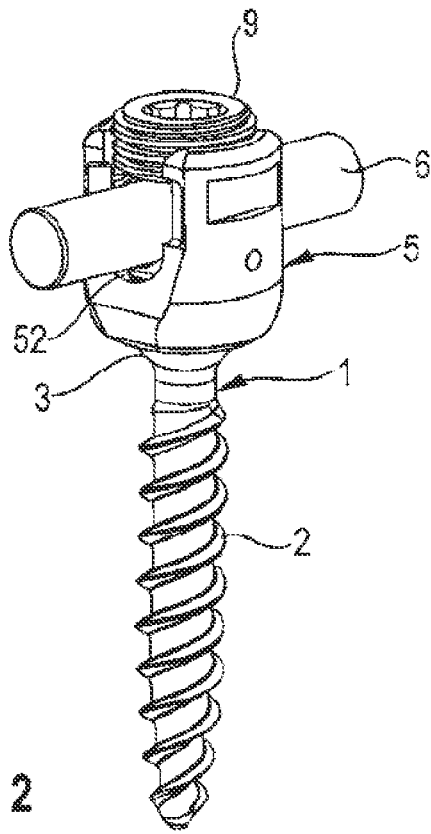
FIG. 2 shows a perspective view of the bone anchoring device of FIG. 1 in an assembled state.
Figure 3:
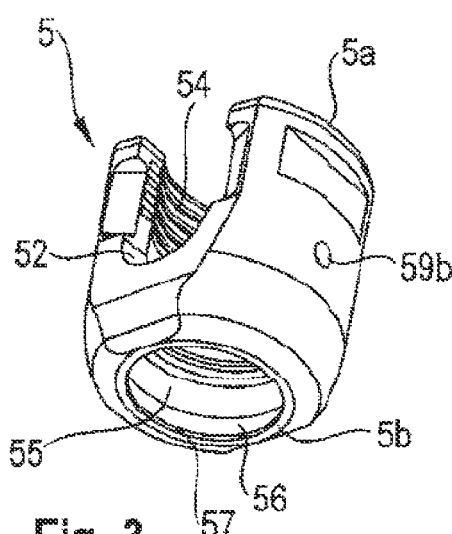
FIG. 3 shows a perspective view of the bottom of a receiving part according to first embodiment.
Figure 4:
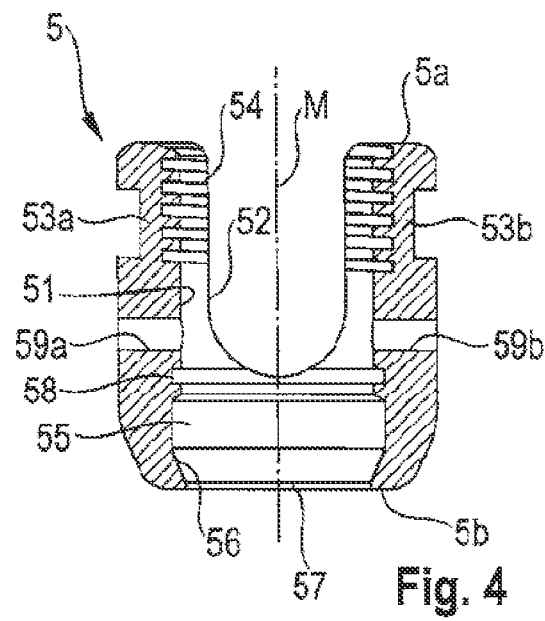
FIG. 4 shows a cross-sectional view of the receiving part shown in FIG. 3, the cross-section taken in a plane through a central axis of the receiving part and perpendicular to an axis of an inserted rod.

As shown in FIGS. 1 and 2, a bone anchoring device according to a first embodiment includes a bone anchoring element 1 in the form of a bone screw having a threaded shank 2 and a head 3, which is in this embodiment a spherical segment-shaped head. The head 3 has a recess 4 for engagement with a screwing-in tool. The bone anchoring device further includes a coupling assembly 10 including a receiving part 5 for receiving a rod 6 to connect the rod 6 to the bone anchoring element 1, and a pressure element 7 for locking the head 3 in the receiving part 5. The pressure element 7 is held in the receiving part 5, for example, via pins 8a, 8b. The rod 6 can be secured in the receiving part 5 via a securing closure element 9, which is in the form of an inner screw in this embodiment.

The receiving part 5 is now explained with reference to FIGS. 1 to 4. The receiving part 5 has a top end 5a and an opposite bottom end 5b and an axis of symmetry M passing through the top end 5a and the bottom end 5b. A bore 51 is provided, which is coaxial with the axis of symmetry M. In a first region adjacent to the top end 5a, the receiving part 5 has a U-shaped recess 52, which is symmetric with respect to a plane including the axis of symmetry M, the recess 52 having a bottom directed towards the bottom end 5b and two free lateral legs 53a, 53b extending towards the top end 5a. In the region of the legs 53a, 53b, an internal thread 54, which cooperates with the inner screw 9, is provided. A channel formed by the U-shaped recess 52 is sized so as to receive the rod 6 therein to connect a plurality of similar anchoring devices. The bore 51 is followed in a direction towards the bottom end 5b by an enlarged accommodation space 55 with a portion having a greater inner diameter than the bore 51, where the accommodation space 55 is intended to accommodate the head 3 and a portion of the pressure element 7, as further explained below. The accommodation space 55 includes a tapered section 56 that tapers and narrows towards the bottom end 5b. The accommodation space 55 opens towards the bottom end 5b via an opening 57 that has an inner diameter greater than a largest outer diameter of the head 3, so that the head 3 is insertable into the receiving part 5 from the bottom end 5b. The bore 51 forms a passage that connects the open top end 5a of the receiving part 5 with the accommodation space 55.

At a distance from the bottom end 5b that corresponds approximately to the position of the bottom of the U-shaped recess 52, an annular groove 58 is further provided in the inner wall of the bore 51. The depth of the groove 58 is such that the inner diameter of the receiving part 5 at the groove 58 is greater than the inner diameter of the bore 51. The inner diameter of groove 58 may be as large as an inner diameter of the accommodation space 55. The groove 58 is configured to receive a retainer ring 11, as explained further below.

On each leg 53a, 53b, bores 59a, 59b are respectively provided for receiving the pins 8a, 8b. The bores 59a, 59b are located approximately at a center of each leg in a circumferential direction and at a position above the groove 58, and farther away from the bottom end 5b.

Figure 5:
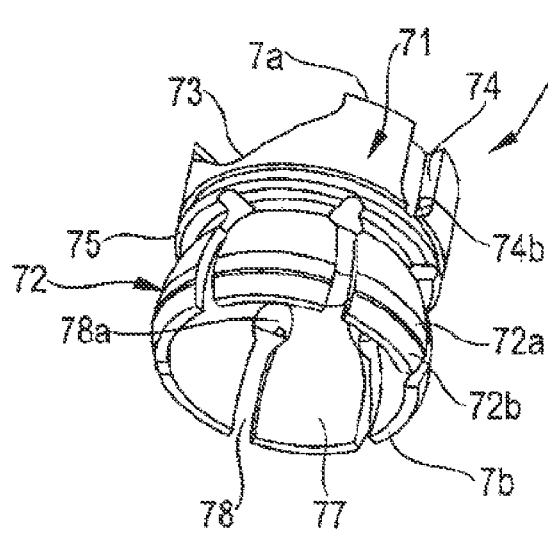
FIG. 5 shows a perspective view from the bottom of a pressure element of the first embodiment.
Figure 6:
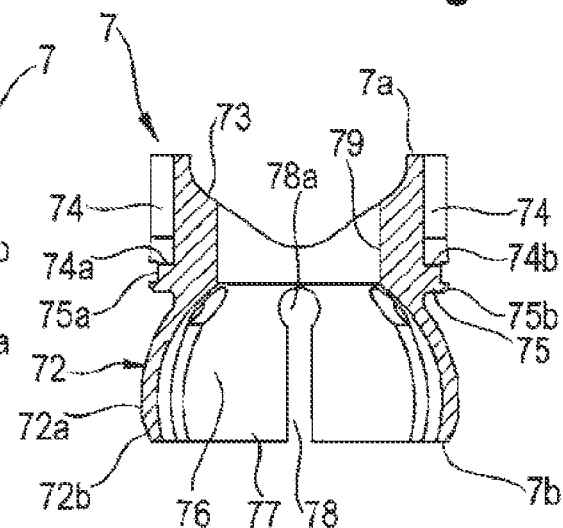
FIG. 6 shows a cross-sectional view of the pressure element shown in FIG. 5, the cross-section taken in a plane through a central axis of the pressure element and perpendicular to an axis of an inserted rod.
Figure 7:
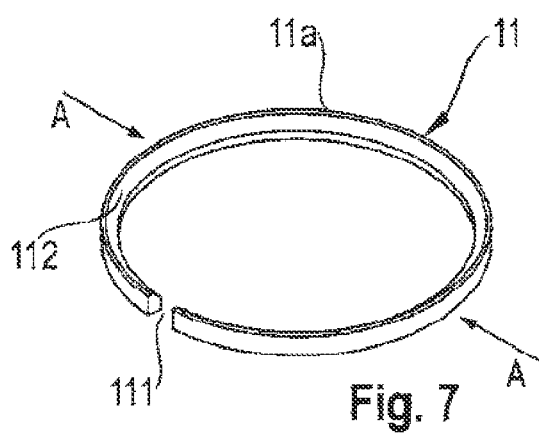
FIG. 7 shows a perspective view of a retaining member of the first embodiment.
Figure 8:
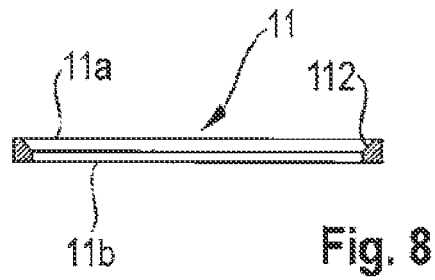
FIG. 8 shows a cross-sectional view of the retaining member shown in FIG. 7 along line A-A in FIG. 7.

Referring to FIGS. 1 and 5 to 6, the pressure element 7 has a top end 7a and a bottom end 7b, a first portion 71 that is substantially cylindrical and that has an outer diameter slightly smaller than the inner diameter of the bore 51 of the receiving part 5, so that the pressure element 7 is movable in the bore 51. The pressure element 7 further includes a second cap-like portion 72 having at least a region that is recessed with respect to the first portion 71, and that has a maximum outer diameter which is smaller than an inner diameter of the largest part of the accommodation space 55. The first portion 71 has at its end opposite to the second cap-like portion 72 a substantially V-shaped recess 73 for receiving the rod 6 therein, when the pressure element 7 is situated in the receiving part 5. The substantially V-shaped recess 73 permits insertion of rods 6 having different diameters, because for typical rod diameters, the contact area of the rod with the pressure element 7 will be along two lines for each rod, regardless of the diameter of the rod. At the lateral sides of the first portion 71 defining the substantially V-shaped recess 73, the pressure element 7 has two elongate recesses 74 in its outer wall, which are arranged opposite to each other, and which are aligned such that a longer side of the elongate recesses 74 is parallel to the axis of symmetry M of the receiving part 5 when the parts are assembled together. The recesses 74 are open towards the top end 7a, and their bottoms 74a, 74b provide stops for the pins 8a, 8b when the pins 8a, 8b are inserted into the bores 59a, 59b and extend slightly into the bore 51. At the end of the first substantially cylindrical portion 71 that faces the cap-like portion 72, there is a circumferentially extending free edge 75 that is formed by a circumferentially extending groove 75a arranged at a height of approximately the bottoms 74a, 74b of the recesses 74. The free edge 75 includes a slanted lower surface 75b that is slanted towards the axis of symmetry M and narrows towards the bottom end 7b. The slanted surface portion 75b is configured to cooperate with the retainer ring 11.

The second, cap-like portion 72 has a first end at the side of the first portion 71, which is recessed with respect to the first portion 71 and a second end that makes up the second end 7b of the pressure element 7. Through the cap-like shape, a hollow interior 76 is provided that is substantially spherically-shaped to clamp a spherical head 3 therein. At the second end 7b, an opening 77 for inserting the head 3 is formed. An outer wall of the second portion 72 includes a spherical first portion 72a and a second tapered portion 72b adjacent to the opening 77. The tapered second portion 72b of the pressure element 7 cooperates with the tapered portion 56 of the receiving part. The second portion 72 of the pressure element 7 further has a plurality of slits 78 extending from an edge of the opening 77 through the second portion 72. The number and dimensions of the slits 78 are such that the wall of the second portion 72 is flexible enough to snap onto the head 3 when the head 3 is being inserted. The closed ends 78a of the slits 78 may be widened with, for example, a circular contour to increase the flexibility of the cap-like second portion 72. The inner diameter of the cap-like portion 72, either as a whole or only in a section adjacent to the bottom end 7b, may be such that the inner diameter of the cap-like portion 72 has a slight undersize with respect to the size of the head 3, so that the head 3 can be clamped by the cap-like portion 72 by friction. The pressure element 7 also has a coaxial bore 79 for providing access to an inserted screw head 3 by a tool.

The pressure element 7 is a monolithic piece. This contributes to a simple design as only one part is required to clamp the head 3 and to receive the rod 6. Furthermore, the first portion 71 of the pressure element 7 is designed as a solid, non-resilient portion that is configured to cooperate with a resilient part, such as the retainer ring 11, to provide a counter-force that deforms the corresponding resilient portion, as explained further below.

The retainer ring 11 has a top end 11a and an opposite bottom end 11b, and a slit 111 extending through the retainer ring 11 from the top end 11a to the bottom end 11b. The slit 111 renders the retainer ring 11 flexible in a radial direction, such that the outer diameter of the retainer ring 11 decreases when the retainer ring 11 is compressed in a radial direction and the slit 111 narrows, and the outer diameter increases when the ring 11 is expanded and the slit 111 becomes larger. An outer diameter of the retainer ring 11 in a non-compressed state is such that, as shown in FIGS. 9 to 10b, the retainer ring 11 is held in the groove 58 of the receiving part 5 with a space between the outside of the retainer ring and the bottom (or outermost wall) of the groove 58, as can be seen in particular in FIG. 10b. The retainer ring 11 further has a slanted inner surface portion 112 that has substantially the same angle with respect to the central axis M as the slanted surface portion 75b of the annular free edge 75 of the pressure element 7. The slanted surface portion 112 of the retainer ring 11 is configured to cooperate with the slanted surface portion 75b of the annular free edge 75 of the pressure element 7. An outer surface of the retainer ring 11 is substantially cylindrical. Because a cross-section of the groove 58 that is configured to accommodate at least a portion of the retainer ring 11 is substantially rectangular, the retainer ring 11 has a corresponding substantially rectangular contour on its outer surface portion to fit into the groove. However, other matching shapes of the cross-sections of the groove 58 and the outer contour of the retainer ring 11 may also be contemplated.

All parts described before may be made of a bio-compatible material, such as a bio-compatible metal like stainless steel or titanium, or of a bio-compatible metal alloy, for example Nitinol, or may be made from a bio-compatible plastic material, for example polyetheretherketone (PEEK). The parts may all be made of the same or of different materials.

The steps of pre-assembling the coupling assembly are explained with reference to FIGS. 9 to 10b. First, the retainer ring 11 is inserted into the groove 58 provided at the inner wall of the receiving part 5. Because the retainer ring 11 is resilient due to its slit 111, ring 11 can be compressed in a radial direction and inserted into the receiving part 5, for example, through the top end 5a. Once the retainer ring 11 has reached the groove 58, ring 11 can expand so that, as shown in the figures, it partially extends into the groove 58. Thereafter, as indicated by the arrow F in FIG. 9, the pressure element 7 is inserted through the top end 5a into the receiving part 5 until the cap-like portion 72 extends into the accommodation space 55. Because the cap-like portion 72 is flexible, it can be compressed, if necessary, in order to be guided through the coaxial bore 51. The pressure element 7 is moved downward until the slanted surface portion 75b of the free edge 75 of the first portion 71 abuts against the slanted surface portion 112 of the retainer ring 11. While in this configuration, shown in FIGS. 10a and 10b, the pins 8a, 8b are inserted into the bores 59a, 59b until they extend into the elongate recesses 74 of the pressure element 7. In this configuration, the pins 8a, 8b provide an abutment for the pressure element 7 that limits an upward movement of the pressure element 7 from an insertion position. Hence, the pins 8a, 8b form a first retaining element that retains the pressure element 7 in the receiving part 5. Simultaneously, in this position, the retainer ring 11 provides an abutment against a further downward movement of the pressure element 7, so that the cap-like portion 72 of the pressure element 7 is held in the accommodation space 55, 56 without contacting the inner wall of the accommodation space 55, 56.

In use, the bone anchoring device is assembled by inserting the head 3 of the bone anchoring element 1 into the receiving part 5 with the inserted pressure element 7. In one embodiment, the bone anchoring device is assembled outside a patient's body, such that a suitable bone anchoring element can be selected prior to surgery according to the specific details of the particular clinical application, and then inserted into the coupling assembly. In another embodiment, a bone anchoring element is inserted into a bone or a vertebra prior to assembling the bone anchoring element with the coupling assembly. The coupling assembly is then mounted in-situ to the implanted bone anchoring element.

Steps of mounting the coupling assembly to the bone anchoring element are described with reference to FIGS. 11 to 15b. First, as shown in FIG. 11, when the pressure element 7 is inserted into the receiving part 5 and held by the pins 8a, 8b, the pressure element 7 is shifted into its uppermost position, which is an insertion position, for allowing the head 3 of the bone anchoring element 1 to be inserted. The insertion position is limited against further upward movement of the pressure element 7 by the abutment provided by the engagement of the pins 8a, 8b with the bottom 74a, 74b of the elongate recesses 74. In the insertion position, the flexible cap-like portion 72 of the pressure element 7 is positioned freely in the accommodation space 55. The head 3 is then inserted through the lower opening 57 of the receiving part 5. Due to the flexibility of the wall provided by the slits 78, the cap-like portion 72 expands in the accommodation space 55 as shown in FIG. 12. The cap-like portion 72 snaps onto the head 3 until it encompasses the head 3 as shown in FIG. 13. The pins 8a, 8b, also prevent the pressure element 7 from escaping through the open top end 5a when the head 3 is inserted and applies an upward force on the pressure element 7 during insertion. In the insertion position, the head 3 is pivotable in the receiving part 5 and is also removable. During the insertion of the head 3, the receiving part 5 may be held by an instrument (not shown).

FIGS. 14a and 14b show the movement of the pressure element 7 into a pre-locking position of the pressure element 7 relative to the receiving part 5. When the head 3 is inserted and the pressure element 7 is pressed down slightly, for example by an instrument, the slanted surface portion 75b of the free edge 75 of the first portion 71 of the pressure element 7 is guided by the slanted surface portion 112 of the retainer ring 11, thereby expanding the retainer ring 11 in a radial direction, so that the retainer ring 11 is further pressed into the groove 58. Simultaneously, the tapered exterior surface portion 72b of the cap-like portion 72 of the pressure element 7 contacts the tapered portion 56 of the accommodation space 55 of the receiving part 5.

A further downward movement of the pressure element 7 into a pre-locking position results in the free edge 75 passing the retainer ring 11 until an upper side 75c of the free edge 75 engages the bottom end 11b of the retainer ring 11. Because of the groove 75a in the first portion 71 of the pressure element 7, the retainer ring 11 has space to contract and can move into the groove 75a. Hence, the bottom end 11b of the retainer ring provides an abutment for the free edge 75 of the pressure element that prevents the pressure element from moving back upwards. Also, in the pre-locking position, the opening 77 of the cap-like portion 72 of the pressure element 7 is configured to be smaller than the opening 57 of the receiving part 5, thereby preventing the head 3 from removal through the lower opening 57 in the pre-locking position. If the cap-like portion 72 has at a section adjacent to the bottom end 7b that has a slight undersize with respect to the head 3, the friction hold of the head 3 can be optimized here, where a certain friction force can be replicated.

In further use, at least two bone anchoring devices are connected through a rod 6. Because of the friction hold of the head 3, the alignment of the receiving parts for taking-up or inserting the rod is more easily facilitated. Finally, the closure element 9 is inserted and tightened, which further presses down the pressure element 7, so that by the engagement of the lower part of the cap-like portion 72 with the receiving part 5, the head 3 is locked in a specific angular position relative to the receiving part 5.

Figure 16:
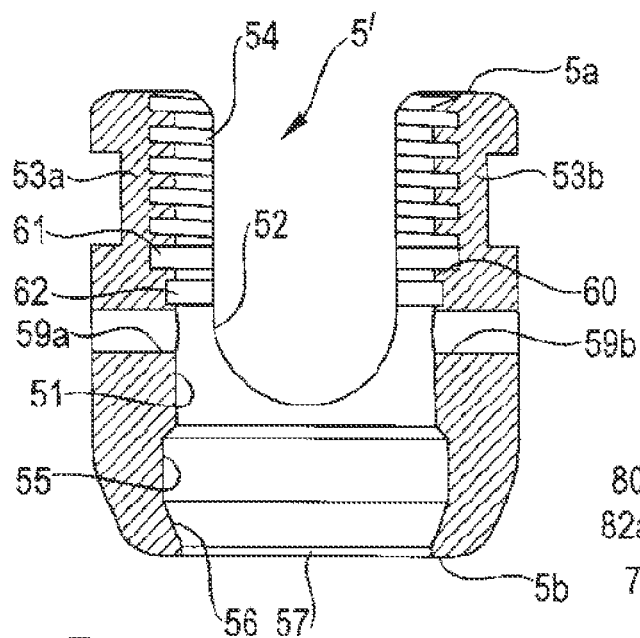
FIG. 16 shows a cross-sectional view of a receiving part according to a second embodiment, the cross-section taken in a plane through a central axis of the receiving part and perpendicular to an axis of an inserted rod.
Figure 17:
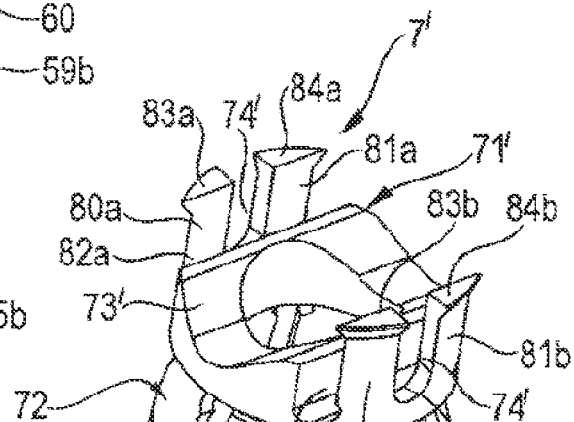
FIG. 17 shows a perspective view of a pressure element according to a second embodiment.
Figure 19:
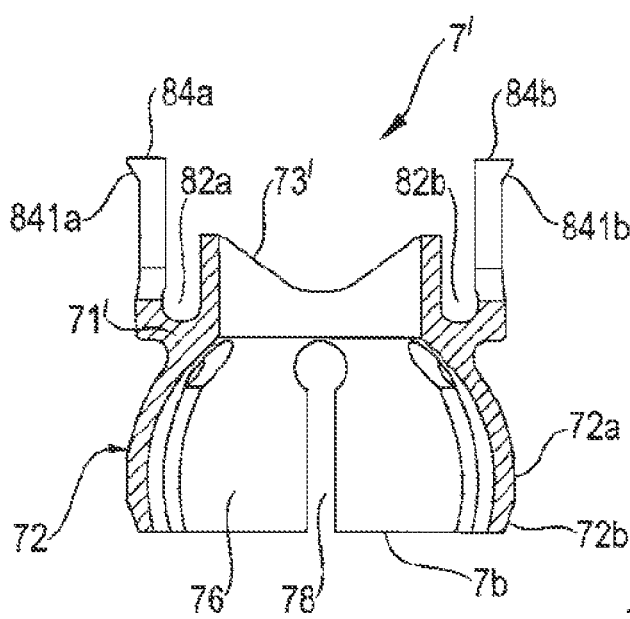
FIG. 19 shows a cross-sectional view of the pressure element shown in FIG. 17, the cross-section taken in a plane through a central axis of the pressure element and perpendicular to an axis of an inserted rod.
Figure 18:
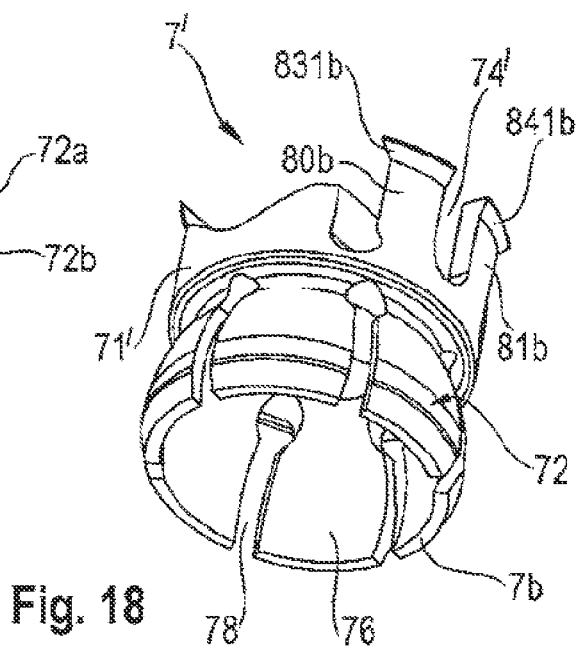
FIG. 18 shows another perspective view of the pressure element shown in FIG. 17.

A coupling assembly according to a second embodiment is shown in FIGS. 16 to 22. The second embodiment differs from the first embodiment in the design of the receiving part and the pressure element. The receiving part 5' does not have a groove 58, but instead includes a retaining element in the form of a projection provided at an inner wall of the receiving part 5'. All other parts and portions that are identical or similar to that of the first embodiment are indicated with the same reference numerals, and the descriptions thereof will not be repeated. The receiving part 5', as shown in FIG. 16, has at a position below the internal thread 54, a projection 60 that extends in a circumferential direction on an inner surface of the legs 53a, 53b. The projection 60 is separated from the internal thread 54 by a first undercut or recessed portion 61 below the internal thread 54, and is further separated from the rest of the coaxial bore 51 by a second undercut or recessed portion 62. An inner diameter of the coaxial bore 51 in the region of the projection 60 is not changed, so that the projection 60 is easy to manufacture. The depth of the undercut 61 corresponds approximately to the root of the internal thread 54, whereas the depth of the undercut 62 may be smaller than the undercut 61, as the undercut 62 serves only as a space for a portion of the pressure element 7' as further explained below.

The pressure element 7' of the second embodiment differs from the pressure element 7 according to the first embodiment in the design of the first portion while the design of the second portion 72 is similar or identical to the first embodiment. The first portion 71' of the pressure element 7' includes on each side of the substantially V-shaped recess 73' two upstanding resilient arms, 80a, 81a and 80b, 81b, that are separated from a central portion that defines the V-shaped recess 73' by a gap 82a, 82b in order to provide flexibility of the arms 80a, 81a, 80b, 81b. The flexible arms 80a, 81a and 80b, 81b extend above the central portion of the first portion 71', and each arm is separated by an elongate recess 74', the bottom 74a', 74b' of which provides an abutment for the pins 8a, 8b. The outer surface portion of the flexible arms 80a, 81a, 80b, 81b may be cylindrical. Each arm 80a, 81a, 80b, 81b has at its free end an outwardly projecting collar portion 83a, 84a, 83b, 84b, which has a substantially circle segment-shaped outer contour in order to fit into the bore 51 when the pressure element 7' is inserted into the receiving part 5'. As can be seen in particular in FIGS. 18 and 19, the lower surface portion 831a, 841a, 831b, 841b of the collar portions 83a, 84a, 83b, 84b are slanted, so as to facilitate smoother movement of the pressure element 7' when the pressure element 7' is inserted into the receiving part 5'. The arms 80a, 81a, 80b, 81b are flexible in such a way that they can be deflected towards the central axis and can resiliently move back to their upright positions. The dimensions of the flexible arms 80a, 81a, 80b, 81b are such that when the pressure element 7' has been inserted into the receiving part 5' and the pins 8a, 8b engage the bottom 74a', 74b' of the elongate recesses 74', the collar portions 83a, 84a, 83b, 84b extend into the first undercut 61.

In the pre-assembled state, the pressure element 7' has been inserted into the receiving part 5' and the pins 8a, 8b are inserted and engage the elongate recesses 74' so that the pressure element 7' can not inadvertently move out through the top end 5a of the receiving part 5'.

Figure 20:
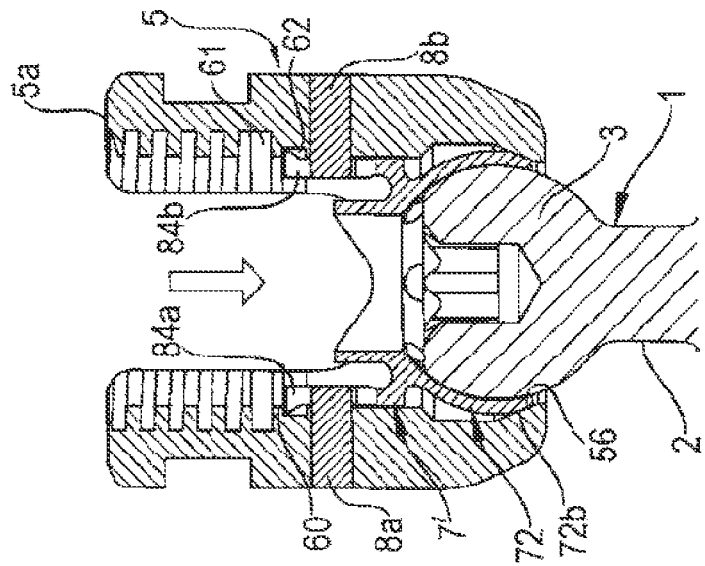
FIG. 20 shows a cross-sectional view of a step of inserting a head of a bone anchoring element into a pre-assembled receiving part with the pressure element according to the second embodiment.
Figure 21:
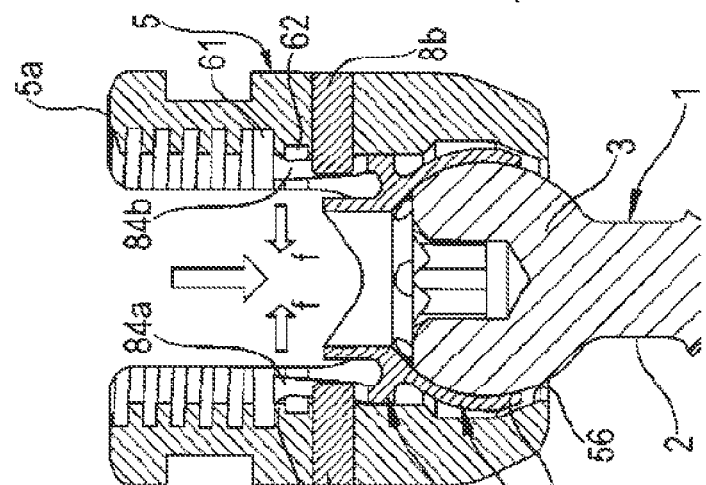
FIG. 21 shows a cross-sectional view of moving the pressure element downward with the head inserted according to the second embodiment.
Figure 22:
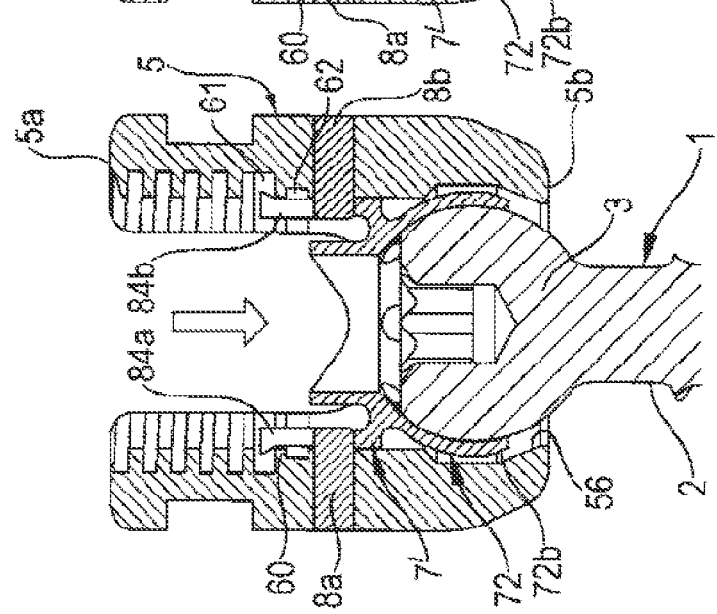
FIG. 22 shows a cross-sectional view of the coupling assembly with the pressure element in the pre-locking position and the head inserted according to the second embodiment.

Referring now to FIGS. 20 to 22, the insertion and pre-locking of the bone anchoring element is explained. First, as depicted in FIG. 20, the pressure element 7' is in an insertion position and the head 3 has already been inserted into the receiving part 5' and into the cap-like portion 72 of the pressure element 7'. During insertion of the head 3, the pressure element 7' is moved upward until the bottoms 74a', 74b' of the elongate recesses 74' abut against the pins 8a, 8b. Hence, the pins 8a, 8b provide a first retaining element to retain or hold the pressure element 7' in the insertion position. Thereafter, the pressure element is moved downward, for example by an instrument, whereby the flexible arms 80a, 81a, 80b, 81b slide with the slanted surfaces 831a, 841a, 831b, 841b of the collar portions 83a, 84a, 83b, 84b along the projection 60. By means of this, the projection 60 compresses the flexible arms 80a, 80b, 81a, 81b towards each other as shown by the transverse arrows f in FIG. 21. Further downward movement of the pressure element 7' moves the collar portions 83a, 84a, 83b, 84b under the projection 60 in the receiving part 5', so that the collar portions 83a, 84a, 83b, 84b can expand into the second undercut 62 of the receiving part 5'.

Simultaneously, the tapered outer surface portion 72b of the cap-like portion 72 of the pressure element 7' engages the tapered section 56 of the accommodation space of the receiving part 5'. This pre-locking position of the receiving part 7' is maintained by the abutment provided by the projection 60 that prevents an upward movement of the pressure element 7' relative to the receiving part 5'. Hence, the projection 60 acts as a second retaining element. Here, in the pre-locking position, the head 3 cannot be removed from the receiving part 5', because the lower opening of the cap-like portion 72 of the pressure element 7' is configured to be smaller than the opening 57 of the receiving part 5'.

A third embodiment of the coupling assembly is described with reference to FIGS. 23 to 25. The coupling assembly in the third embodiment differs from the coupling assemblies in the first and second embodiments in the design of the receiving part and the pressure element. Parts and portions of the receiving part and the pressure element that are identical or similar to the first and second embodiment are indicated with the same reference numerals, and the descriptions thereof will not be repeated. The receiving part 5" has, instead of a continuous cylindrical bore 51, an internal hollow conically-shaped portion 120 that widens towards the top end 5a, as shown in FIG. 23. The hollow conically shaped portion 120 extends between a position corresponding to approximately the bottom of the U-shaped recess 52 and a position below the internal thread 54 of the receiving part 5". By means of this, an undercut portion 120a below the end of the internal thread 54 is provided. Simultaneously, the crest of the last turn of the internal thread 54 provides a projection 60" that serves as an abutment for flexible arms of the pressure element 7".

The pressure element 7" includes, in the first main portion 71" on each side of the V-shaped recess 73", two upstanding flexible arms 80a", 81a" and 80b", 81b". The flexible arms 80a", 80b", 81a", 81b" extend conically outward from the rest of the main portion 71" with a size and cone angle corresponding to the conical section 120 of the receiving part 5". The flexible arms 80a", 81a", 80b", 81b" have a conical outer surface portion and conical inner surface portion, and are thin enough so that they can be flexed inward when a compression force acts on them. As in the second embodiment, the flexible arms 80a", 81a", 80b", 81b" are separated from the central section of portion 71" that defines the V-shaped recess 73" by a gap 82a", 82b".

In use, when the pressure element 7" is inserted from the top end 5a into the receiving part 5", the flexible arms 80a", 81a", 80b", 81b" are compressed and flexed inward. In an insertion position (not shown in the figures), the flexible arms are compressed and extend into the region with the internal thread 54, while the pins 8a, 8b secure the pressure element 7" from moving upward. To move the pressure element 7" to the pre-locking position, the pressure element 7" is moved further downward until the flexible arms 80a", 81a", 80b", 81b" snap into the undercut portion 120a below the projection 60" provided by the internal thread 54. In this pre-locking position, the cap-like portion 72 engages the lower portion 56 of the accommodation space 55 and a removal of the head 3 through the lower opening 57 of the receiving part 5" is prevented.

Further modifications of the embodiments shown may be contemplated. For example, the head of the bone anchoring element can have any other shape, such as a cylindrical shape, whereby a monoaxial bone screw is provided allowing rotation of the screw element with respect to the receiving part around a single axis. In another modification, an uni-planar configuration may be contemplated, where the cap-like portion of the pressure element and the head are defined so as to allow pivoting in only a single plane.

The pressure element according to the second and third embodiments may have one flexible arm on each side or more than one flexible arm on each side. For example, the pressure element according to the second embodiment may have recesses 74' that are closed towards the top end 7a. This would result in one flexible arm on each side with an increased top surface area on each of the arms.

While pins are shown for realizing the first retaining element, the first retaining element can also be otherwise realized or implemented, for example, through crimping. Other modifications, such as flexible elements to retain the pressure element in the insertion position, may also be contemplated.

For the bone anchoring element, any bone anchoring element can be used, such as, for example, bone anchors with threads, with barbs, cannulated bone anchors, two-part bone anchors where the head and the shank are separate parts, etc.

For holding the head in a pre-locking position, the shape of the lowermost section of the accommodation space near the bottom opening of the receiving part and the shape of the lowermost section of the pressure element can be designed, for example, to be rounded or straight, rather than tapered.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A coupling assembly for coupling a rod to a bone anchoring element, the coupling assembly comprising:
    a receiving part with a first end and an opposite second end below the first end, a recess at the first end for receiving the rod, and an accommodation space for accommodating a head of the bone anchoring element, the accommodation space defining an opening at the second end for inserting the head;
    a pressure element positionable at least partially in the accommodation space, the pressure element comprising a first portion configured to engage the head and a second portion configured to engage the rod; and
    a resilient ring separate from the pressure element that is configured to extend more than halfway around the central axis in a circumferential direction, wherein at least part of the ring is configured to extend to an axial position that is lower than a bottom of the recess for the rod;
    wherein when the coupling assembly is at an insertion position, the head is insertable into the accommodation space through the opening at the second end of the receiving part;
    wherein when the coupling assembly is at a pre-locking position, the head is restricted from being removed through the opening at the second end of the receiving part, while the ring restricts the coupling assembly from being adjusted back towards the top end in the insertion position; and
    wherein when the coupling assembly is at a locking position, the pressure element exerts a force directly on the head to lock the head relative to the receiving part.

2. The coupling assembly of claim 1, wherein the ring is a slit ring.

3. The coupling assembly of claim 1, wherein the coupling assembly is adjustable from the insertion position to the pre-locking position only once.

4. The coupling assembly of claim 1, wherein the ring is compressible radially relative to the central axis.

5. The coupling assembly of claim 1, wherein the ring is configured to directly engage the pressure element.

6. The coupling assembly of claim 1, wherein when the coupling assembly is at the insertion position, an expandable portion of the coupling assembly is expandable radially relative to the central axis to facilitate the insertion of the head into the accommodation space, and wherein when the coupling assembly is at the pre-locking position, the expandable portion is restricted from expanding to restrict removal of the head from the accommodation space.

7. The coupling assembly of claim 6, wherein the expandable portion is formed on the pressure element.

8. The coupling assembly of claim 6, wherein at the pre-locking position, the ring restricts axially upward movement of the expandable portion relative to the receiving part.

9. The coupling assembly of claim 1, wherein at least part of the ring is configured to remain at a same axial position relative to the receiving part in the insertion and pre-locking positions.

10. A coupling assembly for coupling a rod to a bone anchoring element, the coupling assembly comprising:
a receiving part with a first end and an opposite second end below the first end, a recess at the first end for receiving the rod, and an accommodation space for accommodating a head of the bone anchoring element;
a pressure element positionable at least partially in the accommodation space, the pressure element comprising a first portion configured to engage the head and a second portion configured to engage the rod; and
a resilient ring separate from the pressure element that is compressible radially relative to the central axis, wherein at least part of the ring is configured to extend to an axial position that is lower than a bottom of the recess for the rod;
wherein when the coupling assembly is at an insertion position, an expandable portion of the coupling assembly is expandable radially relative to the central axis to facilitate insertion of the head into the accommodation space;
wherein when the coupling assembly is at a pre-locking position, the expandable portion is restricted from expanding to restrict removal of the head from the accommodation space, while the ring restricts the coupling assembly from being adjusted back towards the insertion position;
wherein when the coupling assembly is at a locking position, the pressure element exerts a force directly on the head to lock the head relative to the receiving part.

11. The coupling assembly of claim 10, wherein the ring is configured to directly engage the pressure element.

12. The coupling assembly of claim 10, wherein when the coupling assembly is at the insertion position, the head is insertable through an opening at the second end of the receiving part into the accommodation space, and wherein when the coupling assembly is at the pre-locking position, the head is restricted from being removed through the opening at the second end of the receiving part.

13. The coupling assembly of claim 10, wherein the expandable portion is formed on the pressure element.

14. The coupling assembly of claim 10, wherein at the pre-locking position, the ring restricts axially upward movement of the expandable portion relative to the receiving part.

15. The coupling assembly of claim 10, wherein at least part of the ring is configured to remain at a same axial position relative to the receiving part in the insertion and pre-locking positions.

16. The coupling assembly of claim 10, wherein the ring is configured to extend more than halfway around the central axis in a circumferential direction.

17. A coupling assembly for coupling a rod to a bone anchoring element, the coupling assembly comprising:
a receiving part with a first end and an opposite second end below the first end, a recess at the first end for receiving the rod, and an accommodation space for accommodating a head of the bone anchoring element;
a pressure element positionable at least partially in the accommodation space, the pressure element comprising a first portion configured to engage the head and a second portion configured to engage the rod; and
a resilient ring separate from the pressure element, wherein at least part of the ring is configured to extend to an axial position that is lower than a bottom of the recess for the rod;
wherein when the coupling assembly is at an insertion position, the head is insertable into the accommodation space;
wherein the pressure element is configured to expand the ring to adjust the coupling assembly from the insertion position to a pre-locking position where the head is restricted from being removed from the accommodation space, while the ring restricts the coupling assembly from being adjusted back towards the insertion position; and
wherein when the coupling assembly is at a locking position, the pressure element exerts a force directly on the head to lock the head relative to the receiving part.

18. The coupling assembly of claim 17, wherein the pressure element is monolithic.

19. The coupling assembly of claim 17, wherein the ring has a surface that is slanted relative to the central axis of the receiving part that is configured to engage the pressure element to facilitate the expansion of the ring by the pressure element.

20. The coupling assembly of claim 17, wherein when the coupling assembly is at the insertion position, an expandable portion of the coupling assembly is expandable radially relative to the central axis to facilitate the insertion of the head into the accommodation space, and wherein when the coupling assembly is at the pre-locking position, the expandable portion is restricted from expanding to restrict removal of the head from the accommodation space.

21. The coupling assembly of claim 20, wherein the expandable portion is formed on the pressure element.

22. The coupling assembly of claim 20, wherein at the pre-locking position, the ring restricts axially upward movement of the expandable portion relative to the receiving part.

23. The coupling assembly of claim 17, wherein when the coupling assembly is at the insertion position, the head is insertable through an opening at the second end of the receiving part into the accommodation space, and wherein when the coupling assembly is at the pre-locking position, the head is restricted from being removed through the opening at the second end of the receiving part.

24. The coupling assembly of claim 17, wherein at least part of the ring is configured to remain at a same axial position relative to the receiving part in the insertion and pre-locking positions.

25. The coupling assembly of claim 17, wherein an abutting surface of the pressure element is configured to expand the ring, and wherein the ring is configured to compress radially when the abutting surface is lower axially than the ring, such that the ring restricts upward movement of the abutting surface at the pre-locking position.

* * * * *

UNITED STATES PATENT AND TRADEMARK OFFICE
CERTIFICATE OF CORRECTION

PATENT NO. : 12,096,963 B2
APPLICATION NO. : 17/376606
DATED : September 24, 2024
INVENTOR(S) : Lutz Biedermann et al.

Page 1 of 1

It is certified that error appears in the above-identified patent and that said Letters Patent is hereby corrected as shown below:

In the Claims

In Column 10, Line 63, in Claim 1, after "towards" delete "the top end in".

Signed and Sealed this
Twenty-first Day of January, 2025

Coke Morgan Stewart
*Acting Director of the United States Patent and Trademark Office*